US012667643B2

(12) United States Patent
Perrin et al.

(10) Patent No.: US 12,667,643 B2
(45) Date of Patent: Jun. 30, 2026

(54) SURGICAL ADHESIVES

(71) Applicant: COHESIVES, Dijon (FR)

(72) Inventors: Bertrand Perrin, Dijon (FR); Natacha Goutay, Paris (FR)

(73) Assignee: COHESIVES, Dijon (FR)

( * ) Notice: Subject to any disclaimer, the term of this patent is extended or adjusted under 35 U.S.C. 154(b) by 613 days.

(21) Appl. No.: 18/005,708

(22) PCT Filed: Aug. 19, 2021

(86) PCT No.: PCT/EP2021/073090

§ 371 (c)(1),
(2) Date: Jan. 17, 2023

(87) PCT Pub. No.: WO2022/038247

PCT Pub. Date: Feb. 24, 2022

(65) Prior Publication Data

US 2023/0277720 A1 Sep. 7, 2023

(30) Foreign Application Priority Data

Aug. 20, 2020 (FR) ...................................... 2008594

(51) Int. Cl.
*A61L 24/04* (2006.01)
*A61L 26/00* (2006.01)

(52) U.S. Cl.
CPC ......... *A61L 24/043* (2013.01); *A61L 26/0052* (2013.01); *A61L 2300/802* (2013.01); *A61L 2400/04* (2013.01)

(58) Field of Classification Search
None
See application file for complete search history.

(56) References Cited

U.S. PATENT DOCUMENTS

| | | | |
|---|---|---|---|
| 2017/0209617 A1 | 7/2017 | Skaria et al. | |
| 2022/0125988 A1* | 4/2022 | Perrin .................. | A61L 24/043 |

FOREIGN PATENT DOCUMENTS

| | | | |
|---|---|---|---|
| EP | 3514213 A1 | 7/2019 | |
| WO | 2008082929 A2 | 7/2008 | |

OTHER PUBLICATIONS

International Search Report and Written Opinion issued on Nov. 22, 2021, in corresponding International Application No. PCT/EP2021/073090, 14 pages.

* cited by examiner

*Primary Examiner* — Jeffrey D Washville
(74) *Attorney, Agent, or Firm* — Maier & Maier, PLLC

(57) ABSTRACT

A composition including a polymerizable monomer with a phosphate or phosphonate function on the one hand and a methacrylate, acrylate, acrylamide or methacrylamide function on the other hand at a concentration of between 5 and 40% by weight relative to the total weight of the composition,—a photoinitiator at a concentration of between 0.5 and 2% by weight, and a photopolymerizable resin.

14 Claims, No Drawings

SURGICAL ADHESIVES

TECHNICAL FIELD

The present invention relates in particular to compositions for use as a surgical adhesive, a surgical sealant, a haemostatic dressing and/or a cutaneous dressing. More particularly, the present invention relates to compositions for use in a process:

as a surgical adhesive for the adhesion of a material to a biological tissue, for the adhesion of biological tissues to one another, for the adhesion of an adhesive or a substance at the surface of a biological tissue, as a surgical sealant, to seal or plug the orifices created by wire or staple suture or by tissue resection (haemostasis, aerostasis, lymphostasis for example), to close an orifice, an incision or a tear in a biological tissue, as a haemostatic to stop bleeding, alone or as a complement to conventional haemostasis techniques such as suturing, compression or electrocoagulation, or as a dressing on a biological tissue to cover and protect a wound.

These compositions can also be used to reinforce a biological tissue, to fix and stabilise a biological tissue, for the treatment of cutaneous lesions.

BACKGROUND

Many surgical techniques implement surgical adhesives. These are primarily used to help achieve surgical haemostasis. Nonetheless, the effectiveness of surgical adhesives in this indication is controversial and other uses such as for aerostasis do not show better results.

Moreover, surgical adhesives have very weak adhesive properties and therefore cannot be used as an adhesive or as a surgical suture. Most of the time, the application of surgical adhesives is done directly on the tissue, with no preparation of the bonding surface. Tissue penetration is low or non-existent, resulting in poor quality bonding. The Applicants have noticed that current adhesives do not stick and do not penetrate into tissues.

In order to address this problem, low-viscosity surgical adhesives have been proposed. These surgical adhesives penetrate more easily into the tissues, which allows obtaining a better quality bonding. Nonetheless, these surgical glues require high concentrations of monomers. Moreover, their chemical nature can cause burns on the affixing site. These compositions are also difficult to use directly by the general public.

Consequently, the present invention suggests providing a new type of surgical adhesives. The compositions and the method according to the invention allow obtaining a cutaneous adhesion level suitable for application by the general public. The selected concentrations enabling rapid initiation and polymerisation in a few tens of seconds, without causing tissue burns.

Moreover, the selected photopolymeris able resins, combined with the polymerisable monomers, confer on the obtained bonding properties of flexibility, good stability over time under the action of physiological liquids (blood, exudates, perspiration), a limitation of the accumulation of perspiration or exudates at the tissue/bonding interface and good water resistance.

SUMMARY

In particular, the present invention relates to compositions comprising:

a polymerisable monomer comprising a phosphate or phosphonate function on the one hand and a methacrylate, acrylate, acrylamide or methacrylamide function on the other hand, a polymerisation initiator, a photopolymerisable resin.

In the context of the present invention, the polymerisable monomer comprising a phosphate or phosphonate function on the one hand and a methacrylate, acrylate, acrylamide or methacrylamide function on the other hand may be referred to as "polymerisable monomer".

Moreover, the present invention relates to a composition according to the invention for use as a surgical adhesive, a surgical sealant, a haemostatic dressing and a cutaneous dressing.

The present invention also relates to a composition according to the invention for use as a surgical adhesive for the adhesion of a material to a biological tissue, for the adhesion of biological tissues to one another, for the adhesion of an adhesive or a substance at the surface of a biological tissue, as a surgical sealant, to seal or plug the orifices created by wire or staple suture or by tissue resection, to seal an orifice, an incision or a tear in a biological tissue, as a haemostatic to stop bleeding, as a dressing on a biological tissue to cover and protect a wound, to reinforce a biological tissue, to fix and stabilise a biological tissue.

The present invention also relates to a composition according to the invention for use as a surgical adhesive for the adhesion of a material to a non-mineralised biological tissue.

The present invention also relates to a composition according to the invention for use as a surgical adhesive for the adhesion of non-mineralised biological tissues to one another.

The present invention also relates to a composition according to the invention for use as a surgical adhesive for the adhesion of an adhesive or a substance at the surface of a non-mineralised biological tissue.

The present invention also relates to a composition according to the invention for use as a surgical sealant to seal or plug the orifices created by wire or staple suture or by tissue resection.

The present invention also relates to a composition according to the invention for use as a surgical sealant to seal an orifice, an incision or a tear in a non-mineralised biological tissue.

The present invention also relates to a composition according to the invention for use as a haemostatic to stop bleeding.

The present invention also relates to a composition according to the invention for use as a surgical adhesive as a dressing on a non-mineralised biological tissue to cover and protect a wound.

The present invention also relates to a composition according to the invention for use as a surgical adhesive to reinforce a non-mineralised biological tissue.

The present invention also relates to a composition according to the invention for use as a surgical adhesive to fix and stabilise a non-mineralised biological tissue.

The Applicants have been able to demonstrate that the compositions featured superior adhesive capacities and innocuousness compared to the compositions of the prior art. Hence, these compositions are particularly suitable for a cutaneous use as a dressing for wounds and/or for the treatment of all cutaneous lesions.

Preferably, said polymerisable monomer is selected from among the group consisting of molecules having the CAS number [14206-25-8], [14235-57-5], [86242-61-7], [932019-41-6], [1980781-17-6], [60161-88-8], [87243-97-8], [1980048-95-0], [918802-80-9], [63411-25-6], 111980064-07-01, [22432-83-3], [1980781-08-5], [252210-28-9], [1114567-37-1], [80730-17-2], [518991-74-7], [87243-96-7], [1980062-84-7], [518991-75-8], [252210-30-3], [22432-84-4], [727415-30-7], [727415-31-8], [784139-89-5] or [1194231-98-5] and mixtures thereof.

Preferably, the polymerisable monomer is of formula I

[Chem 1]

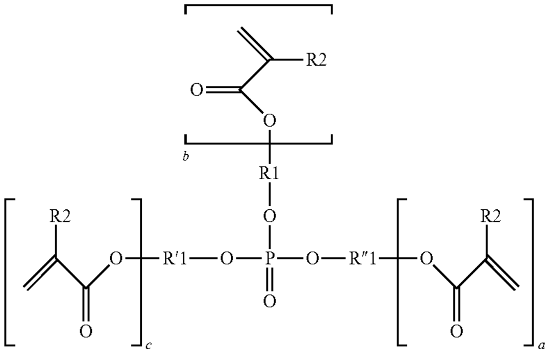

wherein

R2 is H or CH3;

R1, R1', R1" are independently of each other a linear polyether radical, a linear or branched C1-C50 aliphatic radical, a C6-C18 aromatic radical, wherein the carbon chain of said radicals may be interrupted by O, S, OCONH and/or may comprise one or more alcohol function(s);

R1' is H if c=0;

R1" is H if a=0;

b is 1;

a or c is 1 or 0.

The term “the carbon chain of said functions can be interrupted” means that said functions are inserted into the carbon chain, i.e. are bonded to carbon atoms on both sides.

Preferably, a=0, R2=H or CH3 and R'1 and R1 is a linear C1-C12 aliphatic chain.

Even more preferably, a=0, c=0, R2=CH3 and R1 is a linear C1-C12 aliphatic chain.

Preferably, a=0, c=0, R"1=H, R'1=H, R1=linear C1-C12 aliphatic chain, b=1, R2=CH3.

Preferably, a=1, c=1, b=0, R1=H, R'1=R"1=linear C1-C12 aliphatic chain, R2=CH3.

Preferably, the polymerisable monomer of formula I is 10-MDP (C14H27O6P, CAS number [85590-00-7]) or MEP (C12H19O8P, CAS number [32435-46-4]).

According to another preferred embodiment, the polymerisable monomer of formula I is selected from among glycerol dimethacrylate phosphate, ethylene glycol methacrylate phosphate, polyethylene glycol methacrylate phosphate, methacryloyloxy decyl hydrogen phosphate, methacryloyloxy ethyloxy hydrogen phosphate, glycerol monomethacrylate phosphate, triethylene glycol monomethacrylate phosphate, methacryloyloxy propyl phosphate, methacryloyloxy hexyl phosphate, methacrylated aminoethyl phosphonic acid, bis(glyceryl dimethacrylate) phosphate and mixtures thereof.

In the context of the present invention, the term “polymerisable monomer” refers to a monomer whose polymerisation can be initiated by a physical or chemical initiator.

According to a preferred embodiment, the polymerisation is initiated under the effect of a radiation. Preferably, said radiation has a wavelength comprised between 350 nm and 520 nm.

Preferably, the polymer obtained after polymerisation of the monomer is a biocompatible polymer.

According to a preferred embodiment, said viscosity is lower than 120 Pa·s at 20° C.

According to an even more preferred embodiment, said viscosity is lower than 107 Pa·s at 20° C.

According to a quite preferred embodiment, said viscosity is lower than 50 Pa·s at 20° C.

According to a quite preferred embodiment, said viscosity is higher than 20 Pa·s at 20° C.

In particular, the viscosity of the composition can be measured by a falling-ball viscometer according to the standard DIN53015.

According to a preferred embodiment, the composition according to the invention is not a hydrogel.

According to a preferred embodiment, said monomer has a molar mass comprised between 250 and 500 $g \cdot mol^{-1}$.

According to a preferred embodiment, said monomer has a concentration comprised between 5 and 40% by weight relative to the total weight of the composition.

According to an even more preferred embodiment, said monomer has a concentration comprised between 20 and 40% by weight relative to the total weight of the composition.

According to an even more preferred embodiment, said monomer has a concentration comprised between 20 and 40% by weight relative to the total weight of the composition.

According to a quite preferred embodiment, said monomer has a concentration comprised between 25 and 35% by weight relative to the total weight of the composition.

According to a preferred embodiment of the invention, said photopolymerisable resin is selected from among the group consisting of aliphatic urethane acrylate resins, hydrophobic urethane acrylate resins, aromatic urethane acrylate resins, polyether urethane acrylate resins, and mixtures thereof.

According to a preferred embodiment of the invention, said aliphatic acrylate urethane resin is selected from among the group consisting of Allnex Ebecryl 230®, Allnex IRR 907®, Allnex Ebecryl 4491®, Allnex Ebecryl 1271® and mixtures thereof.

According to a preferred embodiment of the invention, said aromatic urethane acrylate resin is Allnex Ebecryl 210®.

According to a preferred embodiment of the invention, said hydrophobic urethane acrylate resin is Dymax Bomar BRC-8435®.

According to a preferred embodiment of the invention, said polyether urethane acrylate resin is Dymax Bomar BR-3641AJ®.

The different resins identified hereinabove confer on the bonding obtained with the composition according to the invention optimum flexibility properties while limiting the exothermics of the polymerisation reaction to an acceptable level.

According to another preferred embodiment, said composition comprises between 50% and 90%, even more preferably between 60 and 80%, by weight relative to the total weight of the composition, of said photopolymerisable resin.

According to a preferred embodiment, the composition according to the invention comprises a polymerisation initiator and even more preferably a photoinitiator. The use of a thermal or redox polymerisation initiator is not excluded from the scope of the present invention. Amongst the redox initiators that can be used, mention may in particular be made of the dibenzoyl peroxide/amine (trimethylaniline) pair.

According to an even more preferred embodiment, said photoinitiator is capable of inducing a polymerisation under the effect of a radiation comprised between 350 and 520 nm.

Preferably, said photoinitiator is selected from among: 2,4,6-trimethylbenzoyl-phenylphosphinate oxide (TPO-L), camphorquinone or 4,4'-bis(diethylamino)benzophenone, the latter associated with Ethyl-4-(dimethylamino)benzoate (EDB), and mixtures thereof.

Advantageously, the photoinitiator is used at a concentration comprised between 0.25 and 2% by weight and preferably between 0.5 and 2% by weight.

According to another preferred embodiment, said composition is free of solvent.

According to a preferred embodiment of the invention, said composition comprises between 0.5 and 2% by weight of said photoinitiator, between 50 and 90% by weight of said photopolymerisable resin, between 20 and 40% by weight of polymerisable monomer.

According to a quite preferred embodiment of the invention, said composition comprises between 0.5 and 2% by weight of TPO-L or camphorquinone associated with EDB, between 50 and 90% by weight of said aliphatic urethane acrylate resin, between 20 and 40% by weight of MDP or MEP.

In the context of the present invention, when the concentrations of the different components of the composition according to the invention are indicated in percentage, it consists of the percentage by weight of said component relative to the total weight of said composition.

In the context of the present invention, the term "comprises" means that the composition according to the invention includes the mentioned elements. Preferably, the present invention relates to compositions comprising only the mentioned elements excluding any other.

The present invention also relates to a method remarkable in that it comprises the steps of:

(i) coating the tissue to be treated with a composition according to the invention, (ii) letting the composition penetrate into said tissue, (iii) inducing the polymerisation of said composition.

According to an embodiment of the invention, step (ii) is optional.

In the context of the present invention, the term "biological tissue" preferably refers to non-mineralised biological tissues.

For clarity, it is specified that, in the context of the present invention, the term "biological tissues" does not refer to bones and teeth.

Preferably, the method according to the invention is non-invasive. The term "non-invasive" means that the method according to the invention does not comprise any surgical step consisting in accessing the tissue to be treated. Thus, the method according to the invention is implemented on a directly accessible biological tissue (for example, the skin) or made accessible beforehand by other methods.

Preferably, the method according to the invention is a non-invasive method for covering and protecting a cutaneous lesion.

Preferably, the method according to the invention is a non-invasive method for bringing the lips of a cutaneous wound close to one another.

Alternatively, the method according to the invention is a method for the adhesion of a material to a biological tissue, for the adhesion of biological tissues together, for the adhesion of an adhesive or of a substance at the surface of a biological tissue, surgical sealing, to seal or plug the orifices created by wire or staple suture or by tissue resection (haemostasis, aerostasis, lymphostasis for example), to seal an orifice, an incision or a tear in a biological tissue, to stop bleeding, to cover and protect a wound, to reinforce a biological tissue or to fix and stabilise a biological tissue.

By "cutaneous", it should be understood a localisation located on the skin, the lips or the oral mucosa.

According to a preferred embodiment, said step (iii) is carried out using an UV radiation or visible light. The characteristics of the implemented radiation, in particular its power and its wavelength, are adapted to the constituents of the composition, in particular to the nature of the polymerisable monomer and to the nature of the polymerisation initiator.

The present invention also relates to a set of parts comprising a composition according to the invention and a radiation source Preferably, the radiation source of the set of parts can emit a radiation adapted to polymerise and/or assist the polymerisation and/or accelerate the polymerisation of the polymerisable monomer of the composition.

In the context of the present invention, the term "radiation source" refers to any artificial means able to produce a radiation with a wavelength comprised between 350 and 520. Preferably, said UV radiation has an irradiance power comprised between 10 $mW/cm^2$ and 100 $mW/cm^2$ and even more preferably between 17 $mW/cm^2$ and 92 $mW/cm^2$.

DETAILED DESCRIPTION

Cutaneous Reaction Test in Humans

Compositions according to the invention have been deposited over the palm. The composition is deposited at the surface of the skin and then polymerised by UV radiation.

The presence or absence of cutaneous reactions are observed during set-up and then in the days that follow.

Optimisation of the Photoinitiator Concentration

Tests have been performed with compositions according to the invention comprising 30% of MEP, 69.5% of Ebecryl 230 and variable concentrations of TPO-L.

A poor hold over time of the bonds and an extension of the photopolymerisation time (>20 s) incompatible with use of the composition are observed for photoinitiator concentrations lower than 0.5%.

An exothermic polymerisation incompatible with use of the compositions in vivo is also observed for concentrations higher than 2%.

Optimisation of the Photopolymerisation Irradiance I0

Tests have been performed with compositions according to the invention comprising 30% of MEP, 69.5% of Ebecryl 230 and 1% of TPOL.

These compositions have been used according to the previously-described protocol and subjected to a radiation with a UV source at 395 nm with variable irradiances.

The lower limit of the irradiance (17 mW/cm2) is limited by the kinetics of polymerisation and the inhibition by oxygen of the reaction. The upper limit of the irradiance (92 mW/cm2) is limited by the exothermic reaction. Nonetheless, irradiance values between 10 and 100 mW/cm2 allow for acceptable results.

Effectiveness of the Compositions According to the Invention

The qualitative evaluation of the In Vivo adhesion and the quality of the bonding has been evaluated on human skin (N=1 to 3 tests). A qualitative adherence scale has been developed:

0: no adhesion at t=0, no anchorage

1: adhesion at t=0, very weak anchorage, detachment in a few minutes, no resistance to stress 2: adhesion at t=0, weak anchorage, hold <1 h, no resistance to stress, rapid detachment on the edges 3: adhesion at t=0, weak anchorage, hold 2 h to 4 h, low resistance to stress, rapid detachment on the edges 4: adhesion at t=0, weak anchorage, hold 4 h to 8 h, low resistance to stress, rapid detachment on the edges 5: adhesion at t=0, average anchorage, hold 4 h to 8 h, average resistance to stress, resistance to detachment on the edges 6: adhesion at t=0, average anchorage, hold 8 h to 12 h, average resistance to stress, resistance to detachment on the edges 7: adhesion at t=0, average anchorage, hold 12 h to 24 h, good to average resistance to stress, good resistance to detachment on the edges 8: adhesion at t=0, good anchorage, hold 24 h to 36 h, good resistance to stress, good resistance to detachment on the edges 9: adhesion at t=0, good anchorage, hold 36 h to 48 h, very good resistance to stress, good resistance to detachment on the edges 10: adhesion at t=0, excellent anchorage, hold >48 h, excellent resistance to stress, no detachment at the edges.

All of the results obtained with the TPO-L+MEP+Ebecryl 230 combination are reported in Table 1.

A statistical processing of these data has revealed a major influence of the concentration of photoinitiator and adhesive monomer on adhesion and holding properties. The higher these concentrations, the greater the adhesive properties will be. On the contrary, low concentrations lead to lower adhesion and holding levels. The irradiance of the LED UV source (at 399 nm) also affects the adhesive properties of the bonds. Moreover, the obtained sensitiveness to water of each of the adhesion layers was compatible with the use of the compositions in the method according to the invention.

TABLE 1

| [TPOL] % wt | (MEP] % wt | [Ebecryl 230] % wt | I0 (mW/cm$^2$) | In vivo hold | Pelage | @ time | Exothermics | Flexibility |
|---|---|---|---|---|---|---|---|---|
| 1 | 30 | 69 | 17 to 20 | 8 | 6.2 | <20 s | +++ | ++ |
| 0.5 | 20 | 79 | 17 to 20 | 3 | N/D | <20 s | 0 | +++ |
| 0.5 | 20 | 79 | 92 | 4 | 1.1 | <20 s | 0 | ++ |
| 0.5 | 40 | 59 | 17 to 20 | 7 | N/D | <20 s | 0 | ++ |
| 0.5 | 40 | 59 | 92 | 6 | 2.3 | <20 s | 0 | + |
| 2 | 20 | 79 | 17 to 20 | 6 | N/D | <20 s | + | +++ |
| 2 | 20 | 79 | 92 | 7 | 0.8 | <20 s | + | ++ |
| 2 | 40 | 59 | 17 to 20 | 8 | N/D | <20 s | +++ | + |

[Table 1] represents the experimental results on the TPOL+MEP+Ebecryl 230 formulation.

The results obtained in Table 2 show that the adhesive monomer concentration can also be lowered to 5%.

TABLE 2

| [TPOL] % wt | (MEP] % wt | [Ebecryl 230] % wt | I0 (mW/cm$^2$) | In vivo hold | @ time | Exothermics | Flexibility |
|---|---|---|---|---|---|---|---|
| 1 | 30 | 69 | 17 to 20 | 8 | <20 s | +++ | ++ |
| 0.25 | 40 | 59.75 | 20 | 2 | 20 s < $t_@$ < 40 s | + | + |
| 0.1 | 40 | 59.9 | 20 | 2 | 40 s < $t_@$ < 60 s | + | ++ |
| 0.5 | 30 | 69.5 | 20 | 5 | <20 s | 0 | ++ |
| 1 | 25 | 74 | 20 | 8 | <20 s | +++ | ++ |
| 1 | 5 | 94 | 20 | 1 | <20 s | 0 | +++ |
| 1 | 10 | 89 | 20 | 2 | <20 s | 0 | +++ |
| 1 | 20 | 79 | 20 | 2 | <20 s | + | ++ |

[Table 2] represents the complementary experimental results on the TPOL+MEP+Ebecryl 230 formulation.

The invention claimed is:

1. A composition as a surgical adhesive for adhesion of a material to a non-mineralized biological tissue, adhesion of non-mineralized biological tissues to one another, adhesion of a glue or a substance at the surface of the non-mineralized biological tissue, as a surgical sealant, to seal or plug orifices created by wire or staple suture or by tissue resection, to seal an orifice, an incision or a tear in the non-mineralized biological tissue, as a hemostatic to stop bleeding, as a dressing on the non-mineralized biological tissue to cover and protect a wound, to reinforce the non-mineralized biological tissue, to fix and stabilize the non-mineralized biological tissue comprising:

between 20% and 40% by weight of a polymerizable monomer, between 0.25% and 2% by weight of a photoinitiator at a concentration comprised between 0.5 and 2% by weight, and between 50% and 90% by weight of a photopolymerizable resin.

2. The composition according to claim 1, wherein said polymerizable monomer is selected from the group consisting of molecules having the CAS number [14206-25-8], [14235-57-5], [86242-61-7], [932019-41-6], [1980781-17-6], [60161-88-8], [87243-97-8], [1980048-95-0], [918802-80-9], [63411-25-6], [1980064-07-0], [22432-83-3], [1980781-08-5], [252210-28-9], [1114567-37-1], [80730-17-2], [518991-74-7], [87243-96-7], [1980062-84-7], [518991-75-8], [252210-30-3], [22432-84-4], [727415-30-7], [727415-31-8], [784139-89-5] or [1194231-98-5] and mixtures thereof.

3. The composition according to claim 1, wherein said polymerizable monomer is of formula I

[Chem 1]

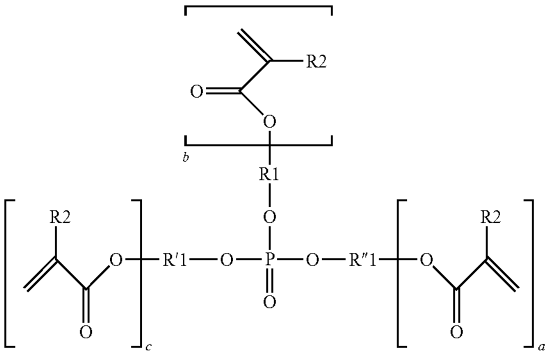

wherein

R2 is H or CH3;

R1, R1', R1" are independently of each other a linear polyether radical, a linear or branched C1-C50 aliphatic radical, a C6-C18 aromatic radical, wherein the carbon chain of said radicals may be interrupted by O, S, OCONH and/or may comprise one or more alcohol function(s);

R1' is H if c=0;

R1" is H if a=0;

b is 1;

a or c is 1 or 0.

4. The composition according to claim 3, wherein a=0, R2=H or CH3 and R'1 and R1 is a linear C1-C12 aliphatic chain.

5. The composition according to claim 4, wherein a=0, c=0, R2=CH3 and R1 is a linear C1-C12 aliphatic chain.

6. The composition according to claim 3, wherein the polymerizable monomer of formula I is 10-(phosphonooxy) decyl methacrylate.

7. The composition according to claim 1, wherein said photoinitiator is configured to induce polymerization under the effect of UV radiation comprised between 350 and 520 nm.

8. The composition according to claim 1, wherein said photoinitiator is camphorquinone associated with Ethyl-4-(dimethylamino)benzoate (EDB).

9. A non-invasive method for covering and protecting a cutaneous lesion, comprising the steps of:

(i) coating the tissue to be treated with a composition according to claim 1, (ii) inducing the polymerisation of said composition.

10. The composition of claim 1, wherein the polymerizable monomer further comprises a phosphate function or a phosphonate function.

11. The composition of claim 1, wherein the polymerizable monomer further comprises a methacrylate function, an acrylate function, an acrylamide function, or a methacrylamide function.

12. The composition according to claim 3, wherein the polymerizable monomer of formula I is bis[2-(methacryloyloxy)ethyl] phosphate.

13. The composition according to claim 7, wherein the UV radiation has an irradiance power between 10 $mW/cm^2$ and 100 $mW/cm^2$.

14. The composition according to claim 13, wherein the UV radiation has an irradiance power between 17 $mW/cm^2$ and 92 $mW/cm^2$.

* * * * *